United States Patent
Yamaguchi et al.

(10) Patent No.: US 7,183,069 B2
(45) Date of Patent: Feb. 27, 2007

(54) REAGENT, METHOD AND APPARATUS FOR MEASURING AMYLASE ACTIVITY

(75) Inventors: Masaki Yamaguchi, Toyama (JP); Hiroshi Yoshida, Osaka (JP); Nobutaka Kusaba, Osaka (JP); Yasufumi Mizuno, Iwata (JP)

(73) Assignees: Toyama University, Toyama (JP); Nipro Corporation, Osaka (JP); Yamaha Hatsudoki Kabushiki Kaisha, Shizouka (JP)

( * ) Notice: Subject to any disclaimer, the term of this patent is extended or adjusted under 35 U.S.C. 154(b) by 465 days.

(21) Appl. No.: 10/383,007

(22) Filed: Mar. 6, 2003

(65) Prior Publication Data

US 2003/0175843 A1 Sep. 18, 2003

(30) Foreign Application Priority Data

Mar. 7, 2002 (JP) ............................ 2002-062094
Jul. 30, 2002 (JP) ............................ 2002-221853

(51) Int. Cl.
   *C12Q 1/40* (2006.01)
(52) U.S. Cl. ........................................................ 435/22
(58) Field of Classification Search .................. 435/22
   See application file for complete search history.

(56) References Cited

U.S. PATENT DOCUMENTS

| | | | |
|---|---|---|---|
| 4,622,295 A | 11/1986 | Ikenaka et al. | |
| 4,810,636 A | 3/1989 | Corey | 435/14 |
| 5,077,011 A | 12/1991 | Amano et al. | 422/56 |
| 5,223,219 A * | 6/1993 | Subramanian et al. | 422/55 |
| 5,334,502 A * | 8/1994 | Sangha | 435/7.21 |
| 5,384,245 A * | 1/1995 | Kwan | 435/22 |
| 2003/0175842 A1 | 9/2003 | Yamaguchi et al. | |

FOREIGN PATENT DOCUMENTS

| | | |
|---|---|---|
| EP | 0 324 912 A2 | 7/1989 |
| EP | 0 459 536 A1 | 12/1991 |
| EP | 0 557 021 A2 | 8/1993 |

OTHER PUBLICATIONS

"Flow-injection-type Biosensor System for Salivary Amylase Activity" Biosensors 2002, May 16, 2002.
"Change of Amylase activity on physical stress test" The Japanese Journal of Stress sciences 29, Oct. 2002 (vol. 16(2)).
"Is Saliva an Index for stress Level?" Iyou densi to seitaikougaku, vol. 39, No. 3 (2002).
"Stress Monitor Via salivary Amylase Activity" CMC syuppankan Monthly Bio Industry-2002 vol. 10 (10) p. 20-25.
"Analysis of stress reaction by salivary α-amylase" Dai 45 kai nihon daekisen gakkai syourokusyu, vol. 42, 2001, p. 2.
Toyama daigaku kouhousi Tomuzu magazinn, No. 4 winter 2002.
Toyama News Paper Mar. 2, 2001.
Nihon keizai News Paper Mar. 23, 2001.
Yomiuri News Paper May 2, 2001.
Toyama News Paper Apr. 5, 2002.
Kitanihon News Paper Jul. 10, 2002.
Japanese Journal of Clinical Dentistry of Children Apr. 2002 (vol. 7, No. 4) p. 35-39.
Suganuma T et al., "Study of the action of human salivary alpha-amylase on 2-chloro-4-nitrophenyl alpha-maltotrioside in the present of potassium thiocyanate", *Carbohydrate Research*, Elseview Scientific Publishing Company. Amsterdam, NL vol. 303, No. 2, Sep. 5, 1997.
Winn-Deen E S et al., "Development of a direct assay for X-amylase", *Clinical Chemistry*, American Association for Clinical Chemistry, Winston, US vol. 34, No. 10, Oct. 1, 1988.
Chatterton et al., "Salivary α-amylase as a Measure of Endogenous Adrenergic Activity," Clinical Physiology, No. 16, 1996, pp. 433-448.
Speirs et al., "The Influence of Sympathetic Activity of Isoprenaline on the Secretion of Amylase from the Human Parotid Gland," Archives of Oral Biology, vol. 19, 1974, pp. 747-752.
Chrousos et al., "The Concepts of Stress and Stress System Disorders," Journal of the American Medical Association, vol. 267, No. 9, Mar. 4, 1992, pp. 1244-1252.
Majima et al., "Determination of α-amylase using a new blocked substrate (2-chloro-4-nitrophenyl $4^4$-O-β-D-galactopyranosyl-β-maltotetraoside)," Clinica Chimica Acta, 1995, vol. 234, pp. 177-179.
Young et al., "Use of a Competitive Inhibitor in a Kinetic Enzymatic Method for Measuring Ethanol in Serum," Clinical Chemistry, 1987, vol. 33, No. 12, pp. 2296-2298.

* cited by examiner

*Primary Examiner*—Christopher R. Tate
*Assistant Examiner*—Amanda P. Wood
(74) *Attorney, Agent, or Firm*—Kilyk & Bowersox, P.L.L.C.

(57) ABSTRACT

An object of the present invention is to provide a means for measuring amylase activity existing in biological samples such as saliva in a more convenient manner and is particularly to provide a means (reagent for measurement, method for measurement and apparatus) by which a sample containing high concentrations of amylase is measured. There has been found a means (reagent for measurement, method for measurement and apparatus), whereby amylase activity in an amylase sample having a high activity value can be quite conveniently measured by making an oligosaccharide substrate carry on a support in an enzymatic method for measuring amylase activity using a modified oligosacharide substrate, whereupon the present invention has been achieved.

15 Claims, 11 Drawing Sheets

Measurement of intensity of color development, by colorimeter

REAGENT, METHOD AND APPARATUS FOR MEASURING AMYLASE ACTIVITY

The present application claims priorities from Japanese Patent Application Nos. 2002/062094, filed Mar. 7, 2002 and 2002/221853, filed Jul. 30, 2002, both incorporated by reference herein.

TECHNICAL FIELD

The present invention relates to a reagent used for measuring amylase activity and, more particularly, it relates to a reagent for measuring amylase activity in saliva of a subject, to a method for measuring amylase activity using said reagent and to an apparatus therefor. It also relates to a method for testing stress of a subject by a measured value of saliva amylase activity.

BACKGROUND OF THE INVENTION

Amylase (enzyme number: EC3.2.1.1) is secreted from pancreas, salivary gland and so on, and is mostly distributed in salivary gland and pancreas. Besides those, it is known to be present in muscle, ovary and oviduct as well. It is further known that amylase which is exuded from tissues is present in blood and urine. It is known that amylase value in serum, urine or pancreatic juice shows a high value in a part of functional disorders of pancreas or salivary gland and kidney or liver, or neoplastic disease. With regard to a method for measuring such amylase activity, an enzymatic method using a modified oligosaccharide substrate, etc. have been known, and the measurement has been carried out as the changes in absorbance using a spectrophotometer or an autoanalyzer. In the studies in recent years, it has been reported that saliva amylase activity value is correlated to stress of a subject [Japanese journal of medical electronics and biological engineering, 39 (3), p. 234–239 (2001), Masaki Yamaguchi, et al.], and a method for measuring amylase activity value in saliva samples has been demanded. However, in the measurement using a conventional autoanalyzer, there are problems such as apparatus for the measurement is expensive, various preparations are necessary before conducting the measurement and several tens minutes are required for the measurement itself.

Disclosure of the Invention

An object of the present invention is to provide a means for measuring amylase activity that exists in a biological sample such as saliva in a more convenient manner within a shorter period, and is to provide a reagent, a measurement method and a measurement apparatus therefore and also a method for testing stress of a subject utilizing the same.

The present inventors have found that an enzymatic method using a modified oligosaccharide substrate, in which a means wherein an oligosaccharide substrate is carried on a support is introduced and an amylase reaction is conducted on the support followed by reading color development by a color discriminating sensor, makes it possible to measure amylase activity conveniently within a period as short as several tens seconds, whereupon the present invention has been achieved.

Thus, the present invention comprises:

1. A reagent for measuring amylase activity which is measured by an enzymatic method, wherein at least a modified oligosaccharide which is a substrate is carried on a support.

2. The reagent for measuring amylase activity according to the above 1, wherein the support is an organic or inorganic carrier that is water-insoluble.

3. The reagent for measuring amylase activity according to the above 1, wherein the shape of the support is a thin film.

4. The reagent for measuring amylase activity according to the above 3, wherein thickness of the thin film is 100 μm~500 μm.

5. The reagent for measuring amylase activity according to the above 3, wherein the thin film is in white color.

6. The reagent for measuring amylase activity according to the above 3, wherein diffused reflection of the thin film is controlled.

7. The reagent for measuring amylase activity according to the above 1, wherein an amount of the modified oligosaccharide carried on the support is that which corresponds to the amount obtained by dipping the support into a solution containing 2 mmol/L~500 mmol/L of the modified oligosaccharide substrate for about 1 to 5 minute(s).

8. The reagent for measuring amylase activity according to the above 1, wherein the modified oligosaccharide which is a substrate is an oligosaccharide selected from G2, G3, G4, G5, G6 and G7, and the reducing end is modified by chromogen.

9. The reagent for measuring amylase activity according to the above 8, wherein the chromogen is selected from 4-nitrophenol (PNP), 2-chloro-4-nitrophenol (CNP) and 2,4-dichlorophenol (Cl$_2$P).

10. The reagent for measuring amylase activity according to the above 1, wherein the modified oligosaccharide is selected from the followings;

2-chloro-4-nitrophenol-4-O-β-D-galactopyranosyl maltoside (hereinafter, referred to as GAL-G2-CNP), GAL-G4-CNP, GAL-G5-CNP, G5-CNP, G6-CNP, G7-CNP, G5-PNP and G7-PNP.

11. A method for measuring amylase activity, comprising contacting a reagent for measuring amylase activity, where at least a modified oligosaccharide which is a substrate is carried on a support, to a biological sample containing amylase, and measuring a labeling substance which is liberated from the substrate.

12. The method for measuring amylase activity according to the above 11, wherein the biological sample is human saliva, blood or a material derived therefrom.

13. The method for measuring amylase activity according to the above 11, comprising measuring the color reaction of the labeling substance, which is liberated from the substrate, by a color discriminating sensor.

14. The method for measuring amylase activity according to the above 11, comprising measuring the reflected light from the support or the transmitted light through the support.

15. The method for measuring amylase activity according to the above 13 or 14, wherein a light-emitting body as a light source is a light-emitting diode.

16. The method for the measurement according to the above 13, wherein an angle for measuring the reflected light is 0~45°, distance from the object to be measured is 10 mm~30 mm and spot diameter is 1 mm~5 mm.

17. An apparatus for measuring amylase activity used for the method for measuring amylase activity according to the above 16.

18. An apparatus for measuring amylase activity, which carries the following functions;

(1) color reaction of a labeling substance liberated from the reagent for measuring amylase activity where at least a modified oligosaccharide which is a substrate is carried on a support is measured by a color discriminating sensor.

(2) reflected light from the support or transmitted light through the support is measured, (3) light-emitting means as a light source is selected from a light-emitting diode, laser, halogen lamp and tungsten lamp, (4) angle for measuring the reflected light is 0~45°, distance from the object to be measured is 10 mm~30 mm and spot diameter is 1 mm~5 mm.

19. A method for testing stress level of a subject, comprising measuring amylase activity in human saliva by a method for measuring amylase activity that comprises contacting a reagent for measuring amylase activity, where at least a modified oligosaccharide which is a substrate is carried on a support, to a biological sample containing amylase, and measuring a labeling substance liberated from the substrate.

20. An apparatus for measuring stress, comprising a light-emitting means for irradiating light to a reagent for measuring amylase activity where at least a modified oligosaccharide which is a substrate is carried on a support, a light-receiving means for receiving the reflected light from the reagent for the measurement, a color-discriminating means for discriminating color development of the reagent for the measurement on the basis of the received reflected light, and a stress-detecting means for detecting degree of stress on the basis of the result of the color discrimination.

21. The apparatus for measuring stress according to the above 20, where said light-emitting means emits light of a single or plural color(s) and said color-discriminating means carries out discrimination of color development on the basis of the intensity of the reflected light upon irradiation of the light of each color to said reagent for the measurement.

22. The apparatus for the measurement of stress according to the above 21, where the light emitted from said light-emitting means comprises light with a complementary color of that developed by the reagent for the measurement or with a color that is near the complementary color.

23. An apparatus for measuring stress, comprising a light-emitting means for irradiating light to a reagent for measuring amylase activity where at least a modified oligosaccharide which is a substrate is carried on a support, a light-receiving means for receiving the reflected light from the reagent for the measurement, a first memory means for memorizing the information to define the relation between intensity of the received reflected light and degree of the stress, and a stress information producing means for producing an information showing the degree of the stress by referring to the intensity of said received reflected light and the information memorized in said first memory.

24. The apparatus for measuring stress according to the above 23, where the information memorized in said first memory is a conversion table where the intensity of said received reflected light is corresponded to the degree of the stress.

25. The apparatus for measuring stress according to the above 23, where the information memorized in said first memory is an arithmetic process information for calculating the degree of the stress on the basis of the intensity of said received reflected light.

26. The apparatus for measuring stress according to any of the above 23 to 25, comprising further equipping with a temperature sensor which detects outside temperature, wherein said stress information producing means corrects said degree of the stress on the basis of the detected temperature.

27. The apparatus for measuring stress according to any of the above 23 to 26, comprising further equipping with a time measuring means for measuring a reaction time of said reagent for the measurement, wherein said stress information producing means corrects said degree of the stress on the basis of the measured reaction time.

28. The apparatus for measuring stress according to any of the above 23 to 27, where said light-emitting means emits the light of a single or plural color(s), and said first memory means memorizes the information to define the relation between intensity of the reflected light of the receive light in each color and degree of the stress.

29. The apparatus for measuring stress according to the above 28, the light emitted from said light-emitting means comprises light with a complementary color of the color developed by the reagent for the measurement or with a color that is near the complementary color 30. The apparatus for measuring stress according to any of the above 20 to 29, comprising equipping with a second memory means which memorizes an information for said degree of the stress as measured history information.

Figure 1:
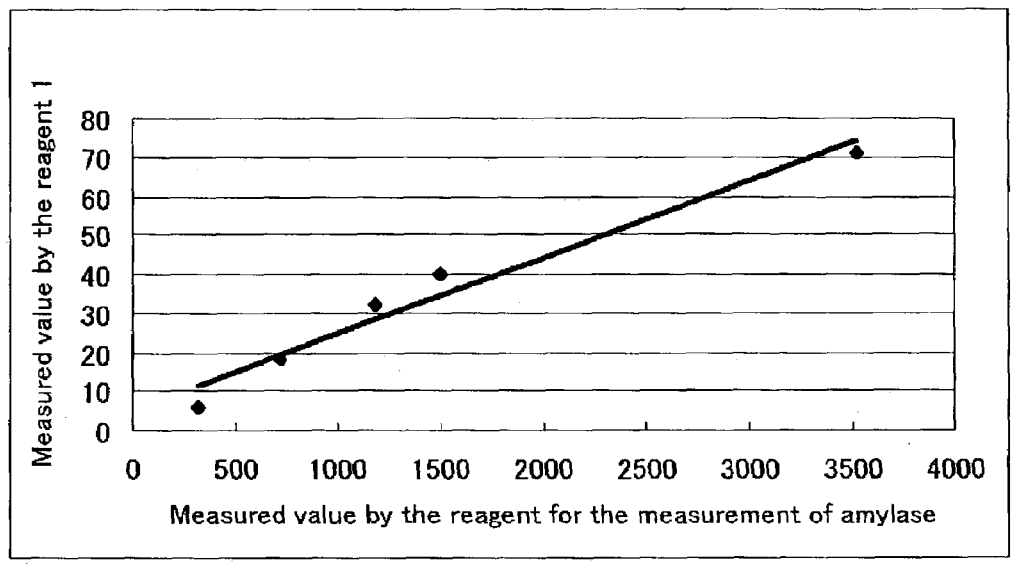
FIG. 1 shows correlation between a result of measurement by Espa Amylase Liquid II and a result of measurement by the reagent 1.

Symbols in the drawings have the following meanings.

| | |
|---|---|
| 1 | body of the apparatus for measurement |
| 6 | slot-forming part |
| 7 | slot |
| 8 | measurement reagent |
| 13 | stress discriminating sensor |
| 15 | optical head |
| 17 | support plate |
| 20 | tap plate |
| 24 | optical head supporting plate |
| 26 | guide plate |
| 27 | projection |
| 61 | guide |
| 64 | projection |
| 101 | semiconductor laser |

| | |
|---|---|
| 110 | light detector |
| 201 | laser driving part |
| 204 | controller |
| 208 | compare operation part |
| 209 | temperature sensor |
| 210 | ROM |
| 211 | memory |
| 111 | optical head |
| 213 | memory card |

BEST MODE FOR CARRYING OUT THE INVENTION

In the present invention, amylase is represented by α-amylase which is mostly secreted from human salivary gland and pancreatic gland. Amylase is a digestive enzyme having a molecular weight of 54,000~62,000 which hydrolyzes polysaccharides such as starch and amylose. It has been known that amylase activity in saliva shows very wide variations depending on one's physical condition and very large personal difference. Although its normal value is around several ten thousands IU/L, it has been known that, even in healthy persons, the value may exceed 100,000 IU/L depending on one's physical condition or habit.

With regard to a substrate used in the present invention for a measurement of amylase activity, a modified oligosaccharide is preferably used. The term "modified" herein means that a compound for labeling which can be discriminated is being linked to the end of, for example, the reducing end of oligosaccharide, and said compound is liberated by amylase or by a coupling enzyme. The numbers of the sugars which comprise said modified oligosaccharide are G2~G7 and, preferably, G2~G5. With regard to the compound for labeling, that which is called chromogen may be generally used and the preferred group is exemplified by 4-nitrophenol (PNP), 2-chloro-4-nitrophenol (CNP) and 2,4-dichlorophenol ($Cl_2P$). Specific examples of the oligosaccharide which is modified with such chromogen are 2-chloro-4-nitrophenol-4-O-β-D-galactopyranosyl-maltoside (hereinafter, referred to as GAL-G2-CNP), GAL-G4-CNP, GAL-G5-CNP, G5-CNP (2-chloro-4-nitrophenyl-maltopentaose), G7-CNP, G5-PNP (p-nitrophenyl-maltopentaose), G6-CNP (2-chloro-p-nitrophenyl-maltotetraose) and G7-PNP. Among those, the particularly preferred ones are GAL-G2-CNP, GAL-G4-CNP and the like where cleavage site upon hydrolysis by amylase is limited to one.

The modified oligosaccharide may be represented by the following formula.

[formula]

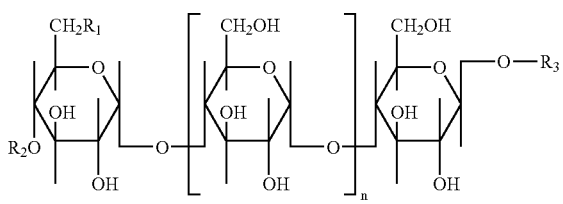

In the formula, $R_1$ and $R_2$ each is hydrogen atom or a protecting group. There is no particular limitation for the protecting group. For example, it is an unsubstituted or substituted lower alkyl group, lower alkoxyl or phenyl group, azide group, halogen atom, N-monoalkylcarbamoyloxy group, alkyl or arylsulfonyloxy group or alkyloxy group, α-glucosyl group, α-maltosyl group and β-galactosyl group. $R_1$ and $R_2$ may be cross-linked each other and said cross-linked group may be further substituted. $R_3$ is a signal-generating group such as a group wherein the signal can be optically detected (preferably, chromogenic aromatic group) and n is 0~5. In the above formula, although —$OR_3$ is in a β-bonded form at position 2 of a glucose having reducing end, it may be in an α-bonded one.

In the reagent for measuring amylase activity according to the present invention, the substrate is carried on a support. Said "carried on a support" means a state where the substrate and the competitive inhibitor is fixed with or trapped by an organic or inorganic carrier that is water-insoluble. With regard to the shape of said support, thin film is advantageous where the thickness is 100 μm~500 μm or, preferably, 150 μm~400 μm. Since color development of the compound for labeling that is liberated is measured by a color discriminating sensor, it is preferred that diffused reflection of light in said thin film is controlled and that the film surface is as uniform as possible. Said thin film is preferred to be in white color. With regard to the material of said thin film, preferred examples are paper, nitrocellulose, Nylon and porous glass, although they are not limited thereto, but many others may be utilized so far as they are able to efficiently carry or hold the substrate that is defined in the present invention.

It is preferred that an amount of said modified oligosaccharide carried on said support is controlled to a constant extent. As a convenient method therefore, there is a method exemplified wherein the support is dipped for about 1~5 minute(s) into a solution containing 2 mmol/L~500 mmol/L of said modified oligosaccharide which is a substrate followed by drying. The corresponding amount obtained thereby exemplifies said amount.

In the measurement method according to the present invention, changes in absorbance by color development of a support for a sample that is caused by liberation of chromogen such as CNP or PNP from a substrate are measured quantitatively, whereby amylase activity is determined. For example, CNP is measured by the absorbance at 405 nm. Usually, the chromogen can be liberated by the action of a great excessive amylase alone. If desired, it is also possible to use a enzyme coupling method comprising a reaction where chromogen is liberated by amylase with α-glucosidase, β-glucosidase or the like after hydrolyzing reaction by amylase. In that case, it is necessary to introduce a means for adding an additional enzyme as a reagent. If further desired, known activators for α-amylase may be used to accelerate the reaction.

Although there is no particular limitation for the reaction temperature in the measurement method of the present invention, it is preferably about 25° C.~40° C. With regard to the reaction time, one to ten and several minute(s) will be sufficient and it depends on the type of the substrate and of the coupling enzyme that is used for the reaction upon necessity.

Figure 3:
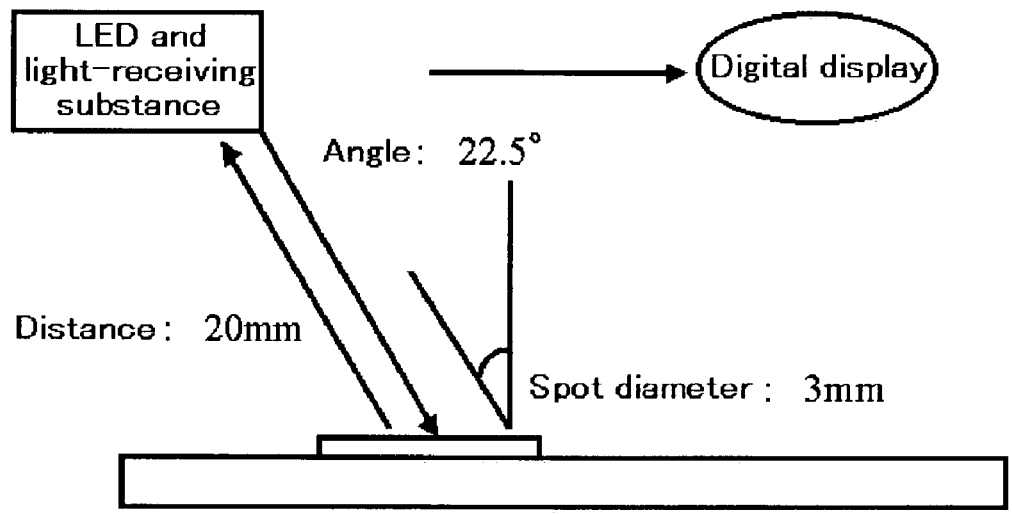
FIG. 3 is a diagram illustrating the apparatus for measurement according to the present invention.

In the measurement of changes by utilizing color development, a color discriminating sensor is appropriately utilized. It is convenient that the changes in color development by a reagent carried on a support are measured by means of reflected light or transmitted light. With regard to a means for emission as a light source, light-emitting diode, laser, halogen lamp, or tungsten lamp, etc. is preferably used, although it is not limited thereto. In the measurement of reflected light, there may appropriately used an apparatus for measurement which satisfies the conditions that angle is 0~45°, preferably 10°~35°, more preferably 15°~30°, and distance from the object to be measured is 10 mm~30 mm, preferably 15 mm~25 mm, more preferably 18 mm~22 mm, and sample spot diameter is 1 mm~5 mm, preferably 2 mm~4 mm, more preferably 2.5 mm~3.5 mm. The concept of the apparatus and of the reagent according to the present invention is shown in FIG. 3.

The method for measuring amylase activity utilizing the reagent of the present invention thus provided is suitable for a sample containing a high concentration of amylase as a biological sample. For example, saliva, blood, urine, etc. may be used as samples and saliva is most preferred.

The present invention, in which a convenient measurement of amylase activity in human saliva can be performed, makes it possible to provide convenient and effective means for a method for detecting the stress level of a subject. To be more specific, α-amylase activity in saliva collected from a subject in a resting period is measured, and the activity value is recorded, memorized and used as a standard value. After that, α-amylase value of the subject at a certain condition is measured and compared with the standard value that was recorded and memorized in a resting period. When the enzymatic activity is higher than the standard value, it is judged that the subject receives unpleasant stress (distress), while, when it is lower than that, he/she is in comfortable conditions. In addition, the more the difference from the standard value, the higher the stress being received is, and the degree of the stress, which body or mentality receives, can be judged.

Further, when α-amylase activity is continuously measured, it is possible to catch the changes in stress with a lapse of time. When one receives distress, there is a rise in the α-amylase activity in saliva. It is possible to judge a degree of extent of the stress from a size of a positive time gradient at that time. On the contrary, in comfortable conditions with little stress, enzymatic activity of α-amylase lowers, so that it is expressed as a negative time gradient whereby the degree of extent can be judged as well.

It is also possible that α-amylase activity is measured with following time and the changes in enzymatic activity caused by stress that has been loaded during the measuring time are grasped whereby a degree of extent of the stress is judged from size of the changes and time consumed for recovering to the value before loading the stress (standard value).

EXAMPLES

The present invention will be illustrated in more detail by way of the following Examples, although the present invention is not limited thereto. All matters will be within a scope of the technical idea of the present invention so far as they relate to a method for measuring amylase activity by an enzymatic method where a modified oligosaccharide which is a substrate is carried on a support.

Example 1

Preparation of Reagent 1 (Test Paper)

Advantec Filter Paper 514A (Toyo Filter Paper) was dipped for 3 minutes in a solution where 14 mmol/L of Gal-G2-CNP and 700 mmol/L of KSCN were dissolved, and then dried. The resulting test paper was cut into a size of 7 mm×7 mm.

Example 2

A reagent (Test paper) where a substrate and a competitive inhibitor were carried on a support was prepared according to the following method.

Advantec Filter Paper 514A (Toyo Filter Paper) was dipped for 3 minutes in a solution where 70 mmol/L of Gal-G2-CNP, 3.5 mmol/L of KSCN and 1 mol/L of maltotetraose were dissolved in a buffer, and then dried. The resulting test paper was cut into a size of 7 mm×7 mm.

Example 3

A reagent (Test paper) where a substrate and a competitive inhibitor were carried on a support was prepared according to the following method.

Advantec Filter Paper 514A (Toyo Filter Paper) was dipped for 3 minutes in a solution where 140 mmol/L of Gal-G2-CNP, 7 mmol/L of KSCN and 0.5 mol/L of maltopentaose were dissolved in a buffer, and then dried. The resulting test paper was cut into a size of 7 mm×7 mm.

Test Example 1

Measurement of an amylase activity was carried out according to the following treatment using the reagent of Example 1.

1. Amylase activity value of five samples (a to e) which were saliva samples collected from healthy volunteers was measured by Espa Amylase Liquid II (Nipro) which is a reagent for a measurement of amylase activity. Espa Amylase Liquid II is a reagent for measuring amylase activity by an enzymatic method using Gal-G2-CNP and is able to measure amylase to an extent of 2,000 IU/L. For the measurement, an Autoanalyzer 7170 (Hitachi) was used. Since the sample e exceeded the measuring limit, measurement thereof was not possible as it was. Therefore, each of the samples diluted to an extent of 10-fold using 1% (W/V) BSA (meaning a 1% (W/V) solution of bovine serum albumin in physiological saline; hereinafter, this has the same meaning as well) was measured instead. Result of the measurement is shown in Table 1.

TABLE 1

| Measured Values | |
|---|---|
| Sample a | 330 |
| Sample b | 728 |
| Sample c | 1183 |
| Sample d | 1497 |
| Sample e | 3520 |

2. A color discriminating sensor CZ-V1 of Keyence was adjusted so that angle of reflected light was made 22.5°, distance from the object to be measured was made 20 mm and spot diameter was made 2 mm. For the measurement, C mode was used. A drawing of the apparatus is shown in FIG. 3.

3. Measurement of amylase activity value of the samples prepared in was carried out using the reagent 1. The apparatus adjusted in 2 was used for the measurement. A sample (3 μL) was dropped into the reagent 1 and the difference in the measured values by the apparatus between before the reaction and 1 minute after the reaction was calculated. The result is shown in Table 2.

TABLE 2

| Measured Values | |
| --- | --- |
| Sample a | 6 |
| Sample b | 18 |
| Sample c | 32 |
| Sample d | 40 |
| Sample e | 71 |

Correlation between the result of measurement by Espa Amylase Liquid II and the result of measurement by the reagent 1 is shown in FIG. 1. A high correlation with r=0.98 was resulted. When the measured values obtained by the reagent 1 were multiplied by 44, the results were nearly the same as those in the convention method. Thus, it was shown that the reagent of the present invention was able to directly measure the amylase activity value in the sample.

Test Example 2

Measurement of amylase activity using the reagent of Example 2 was carried out in accordance with the following treatment.

1. The sample f which is a saliva sample collected from a healthy volunteer was diluted to an extent of 0.2, 0.4, 0.6 and 0.8-fold using 1% (W/V) BSA.
2. Amylase activity values of the above samples and a negative control sample (physiological saline) were measured by Espa Amylase Liquid II (Nipro) which is a reagent for measurement of amylase activity. For the measurement, Autoanalyzer 7170 (Hitachi) was used. Since the sample was not possible to be measured because it exceeds the measuring limit, each of the samples diluted to an extent of 10-fold using 1% (W/V) BSA was measured instead. Result of the measurement is shown in Table 3.

TABLE 3

| Measured Values | |
| --- | --- |
| Sample f | 328 |
| Sample f x 0.8-fold | 212 |
| Sample f x 0.6-fold | 175 |
| Sample f x 0.4-fold | 147 |
| Sample f x 0.2-fold | 77 |
| Physiological saline | 0 |

3. Measurement of amylase activity value of each sample was carried out using the reagent 1 used in Example 1. The apparatus used in Example 1 was used for the measurement. A sample (3 µL) was dropped into the reagent 1 and the difference in the measured values by the sensor before the reaction and 1 minute after the reaction was measured. The result is shown in Table 4.

TABLE 4

| Measured Values | |
| --- | --- |
| Sample f | 75 |
| Sample f x 0.8-fold | 58 |
| Sample f x 0.6-fold | 42 |
| Sample f x 0.4-fold | 38 |
| Sample f x 0.2-fold | 14 |
| Physiological saline | −2 |

Figure 2:
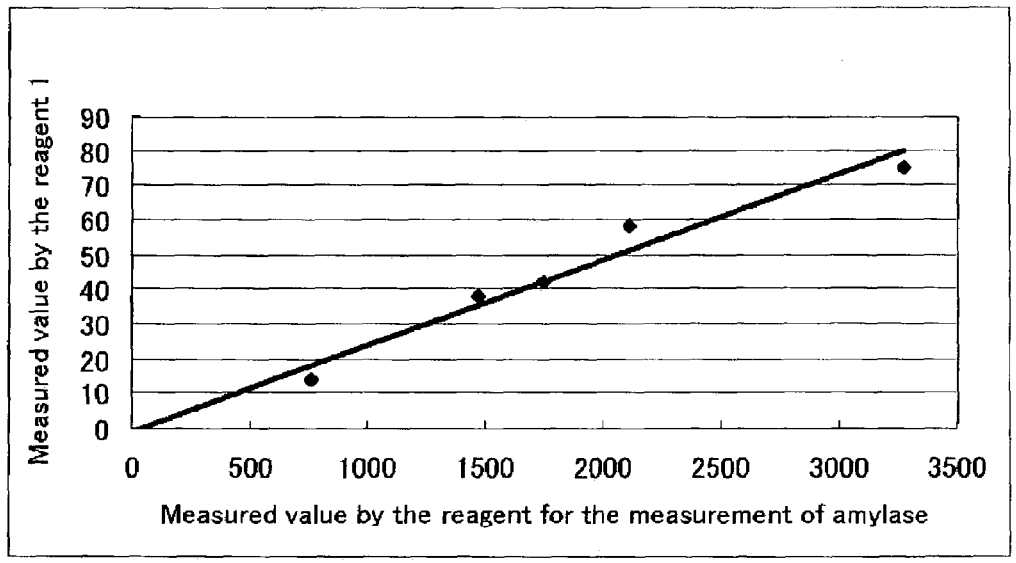
FIG. 2 shows the correlation between a result of measurement by Espa Amylase Liquid II for a 10-fold diluted sample and a result of measurement by the reagent 1.

Correlation between the result of the measurement of 10-fold diluted samples by Espa Amylase Liquid II and the result of the measurement by the reagent 1 is shown in FIG. 2. A high linearity with r=0.99 was resulted.

When the measured value by the reagent 1 was multiplied by 43, the result was nearly the same as that in the convention method. Thus, it was shown that the reagent of the present invention was able to directly measure the amylase activity value in the sample.

Example 4

Now, an example of a constitution of an apparatus for measurement of stress where the above measuring method is utilized will be illustrated.

Figure 4:
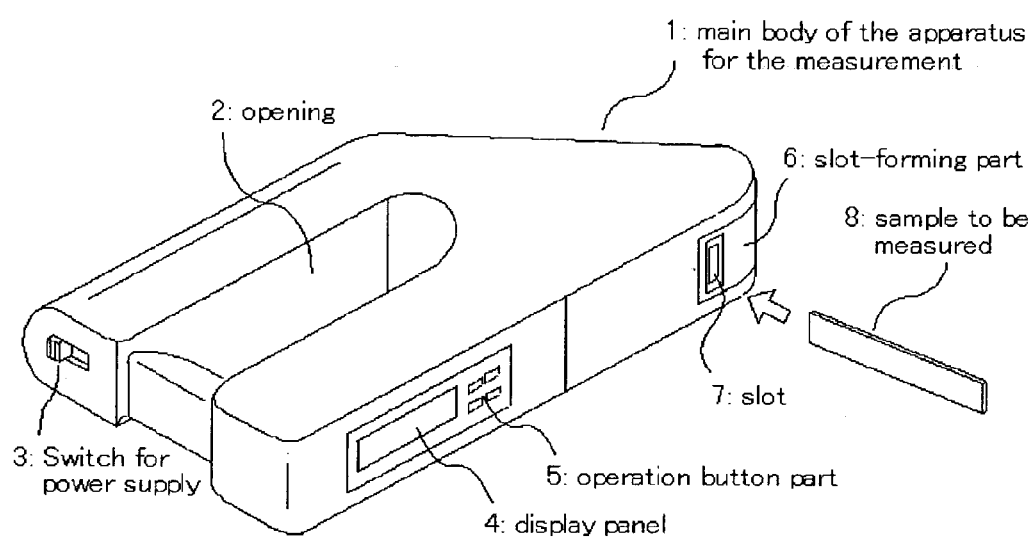
FIG. 4 shows an overview of the apparatus for measurement of stress according to an embodiment.
Figure 5:
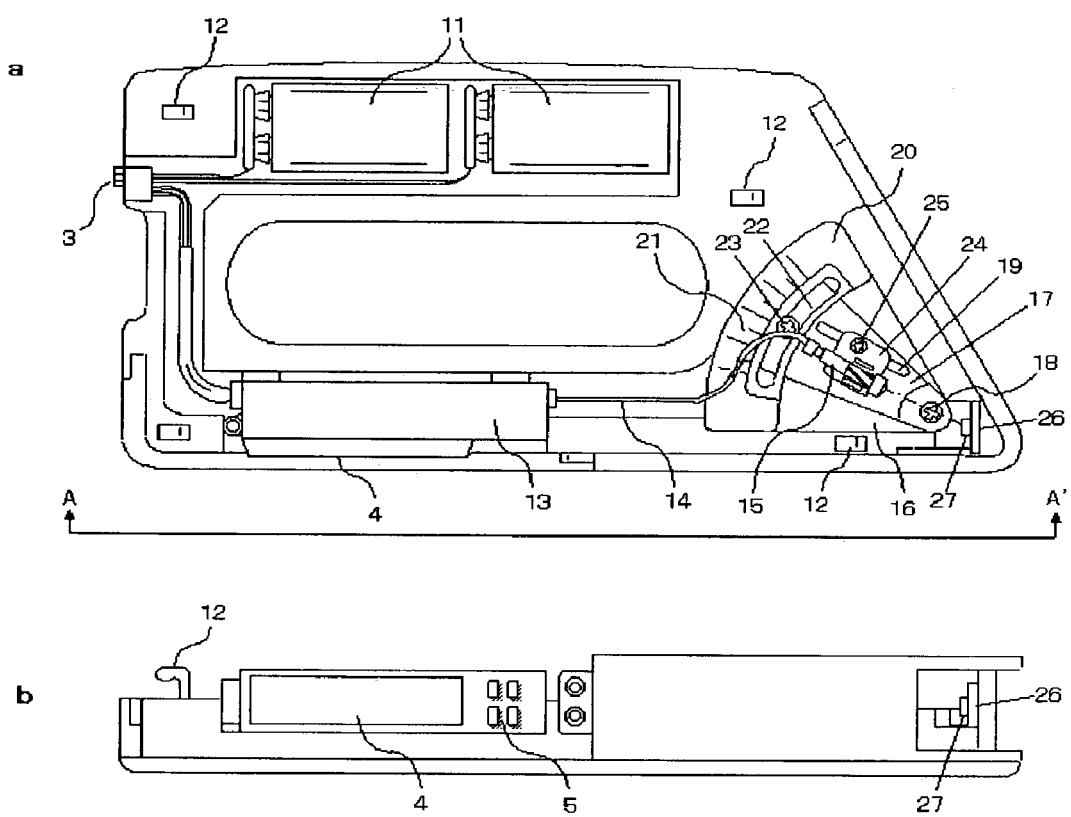
FIGS. 5a and 5b shows the inner structure of the apparatus for measurement of stress according to an embodiment.

FIG. 4 shows an outer constitution of the measurement apparatus. In the main body 1 of the measurement apparatus, an opening 2 is formed in the center, while on the left-hand side face thereof, a switch 3 for power supply is arranged. In front of the main body 1 of the measuring apparatus, there are arranged display panel 4, operation button part 5 and slot-forming part 6 and, on the slot-forming part 6, there is formed a slot 7 for the insertion of a reagent 8 for the measurement.

Incidentally, the reagent 8 for the measurement is formed by a long and slender-plate-shaped paper piece and, in its center, there is formed a rimple for folding the reagent. When the reagent for the measurement is folded along this rimple, its front end touches the reagent-holding part of the measurement reagent 8. The reagent-holding part of the measurement reagent 8 is in white color before the reaction with saliva. After the reaction with saliva, the color of the reagent holding part changes to the color that is developed by a signal generation group used and becomes darker corresponding to the degree of stress. In the above-mentioned example for the measurement, the developed color is in yellow color. According to the signal generation group as mentioned above, the development of other color is also possible.

In conducting the measurement of stress, an initial operation for an adjustment of zero point is carried out according to the following steps before the actual operation for measurement. Firstly, the switch 3 for a power supply is operated to make it on and a standard paper (in white color) is inserted into a slot 7. After that, a button for the adjustment of zero point at the operation button part 5 is operated. As a result, color discrimination of the standard paper is done by the stress discriminating sensor inside and the result of the discrimination is set in the inner memory as an initial value. When setting of the initial value finishes, an indication thereof is done on the display panel 4. After that, the standard paper is pulled out from the slot 7 whereupon the initial operation is completed.

Measurement of stress is carried out as follows. Firstly, the front end of the measurement reagent 8 is licked with the tongue so that saliva is impregnated therein and then the measurement reagent 8 is folded up along the rimple. After that, the position of the reagent-holding part is sandwiched by fingers for a certain period only so that saliva is impregnated in the reagent-holding part. Then, the fold-up measurement reagent 8 is returned to the original position and is inserted into a slot 7 in such a manner that the reagent-holding part turns to the left-hand side of FIG. 4. As a result of such an insertion, discrimination of color of the reagent-holding part is carried out by a stress discriminating sensor inside. Result of the color discrimination is compared with the initially set value obtained by the above-mentioned standard paper. Stress value is calculated depending upon the result of the comparison and is displayed on the display panel 4.

Now, a specific example of constitution of the above-mentioned measurement apparatus will be illustrated by referring to FIGS. 5a and 5b, FIG. 6 and FIG. 7.

Firstly, the inner structure of the measurement apparatus is shown in FIGS. 5a and 5b. FIG. 5a shows the upper surface of the apparatus when a slot-forming part 6 and an upper cover of the measurement apparatus shown in the above FIG. 4 are removed, while FIG. 5b shows its front view.

In the drawing, 11 is a battery for supplying electric power, 12 is a hook for holding the upper cover, 13 is a stress discriminating sensor, 14 is optical fiber which optically connects a light coupling terminal of the stress discriminating sensor 13 to an optical head 15 and 15 is an optical head which irradiates the light (where the light-emitting means is selected, for example, from light-emitting diode, laser, halogen lamp and tungsten lamp) to the reagent-holding part of the above-mentioned measurement reagent 8 and also receives the reflected light thereof.

16 is a fan-shaped hollow part formed on the basement of the main body 1 of the measurement apparatus, 17 is a support plate arranged in the hollow part 16 in a rotatable manner using a screw 18 as a supporting axis, 19 is a guide gutter formed on a support plate 17, 20 is a pressing plate fixed in a hollow part 16 whereby a rotating end of the support plate 17 is pressed from upside, 21 is a scale formed on a pressing plate 20, 22 is a guide gutter formed on a pressing plate 20 and 23 is a screw for fixing a support plate 17 at a predetermined scale position.

24 is an optical head-holding plate which slides along a guide gutter 19 of a support plate 17, 25 is a screw for fixing an optical head-holding plate 24 at a predetermined position, 26 is a guide plate for guiding a slot-forming part 6 and 27 is a column-shaped projection formed on a guide plate 26 for holding a slot-forming part 6 at an arranged position.

When the switch 3 for power supply is made on, the power from the battery 11 is supplied to a stress discriminating sensor 13 and light is emitted from the stress discriminating sensor 13. The light is supplied to an optical head 15 via an optical fiber 14 and is emitted from the front end of the optical head 15. The light is irradiated to the reagent-holding part of the measurement reagent inserted from the slot 6 as mentioned above. The light is absorbed, scattered or reflected at the reagent-holding part and a part of the reflected light moves backward along the optical axis of the optical head 15 and is received by the optical head 15. The light received as such is transmitted to a stress-discriminating sensor 13 via an optical fiber 14. The stress-discriminating sensor 13 analyzes and calculates the intensity of said reflected light as will be mentioned later whereby a stress value is calculated.

Figure 6:
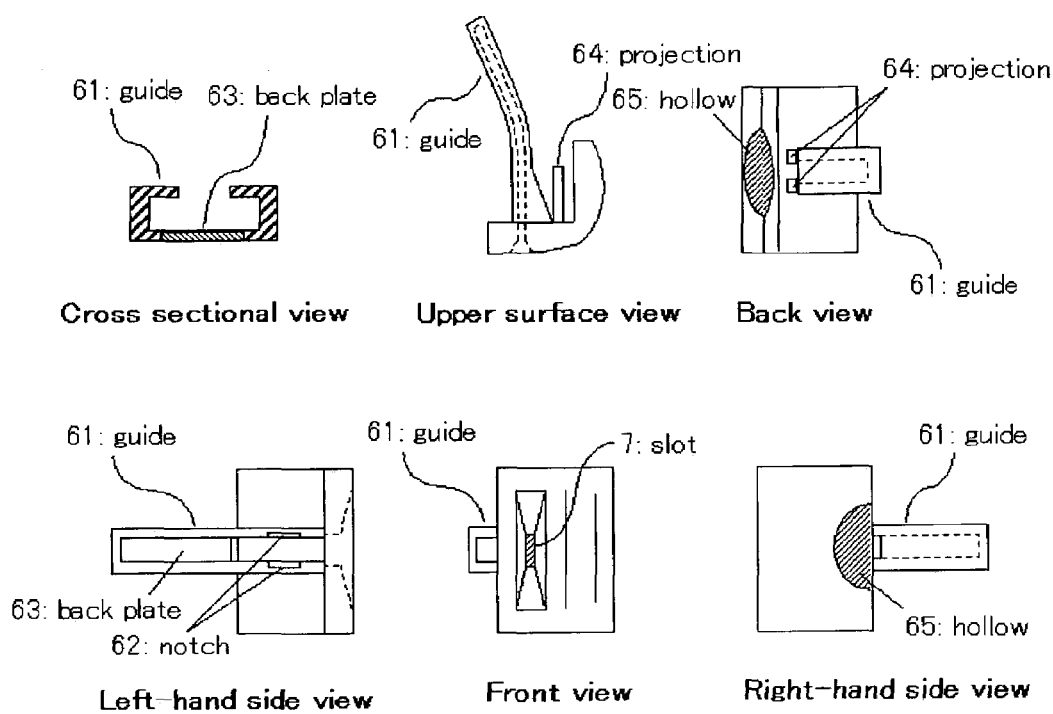
FIG. 6 shows the constitution of a slot-holding part according to an embodiment.

FIG. 6 shows the structure of the above-mentioned slot-forming part 6. Guide 61 is formed on the back side of a slot 7 formed in front of the slot-forming part 6. As shown in the drawing for the upper surface in FIG. 6, the guide 61 is formed in such a manner that, from halfway, it is curved with a predetermined curvature. Therefore, when the measurement reagent 8 is inserted from the slot 7 until the end of the guide 61, the measurement reagent 8 bent along this curve and is compressed to the bottom in the guide 61 due to its resilience. As a result, the measurement reagent 8 is positioned at a predetermined position of the bottom of the guide 61 without displacement in the vertical direction of its plane and also in front and rear direction as well as in right and left direction thereof.

As shown in the left-hand side view in FIG. 6, a notch 62 is formed on the guide 61. The notch 62 is formed near the position where the reagent-holding part is positioned when the measurement reagent 8 is inserted until the final end of the guide 61. As a result of such a notch 62, it is possible to induce the light from the optical head 15 to the reagent-holding part without shielding by the guide. On the guide 61, a back plate 63 is fixed from the position which is slightly before the above-mentioned curved position until the final end of the guide. The back plate 63 has such an effect that the front end of the measurement reagent 8 is guided to the final end of the guide along the above-mentioned curve against the resilience of the measurement reagent 8 caused by the above-mentioned curve.

On the back of the slot-forming part 6, there is formed a pair of projections 64 having hooks at the front end. Such projections 64 act as guides and stoppers when the slot-forming part 6 is attached to the main body 1 of the measurement apparatus. When the slot-forming part 6 is attached to the main body 1 of the measurement apparatus, the slot-forming part 6 is pushed forward from the front of the main body 1 of the measurement apparatus 1 in such a manner that the guide plate 26 of FIG. 5a is inserted into a gap between the outer wall and the projection as shown in the upper surface view of the same drawing. As a result, the front end of the projection 64 attaches the projection 27 of the guide plate 26 and a pair of projections 64 is bent and spread out. When the slot-forming part 6 is pushed forward to the attached position, said pair of projections 64 is elastically reverted to the original position and the hook formed at the front end and the projection 27 of the guide plate 26 are engaged each other. As a result thereof, detachment of the slot-forming part 6 can be prevented whereby the slot-forming part 6 is attached to the main body 1 of the measurement apparatus.

A hollow 64 shown in the right-hand side view and the back side view of FIG. 6 functions as a finger-holding place when the slot-forming part 6 is detached from the main body 1 of the measurement apparatus. In order to detach the slot-forming part 6 from the main body 1 of the measurement apparatus, the hollow 65 is picked at by a finger to pull the slot-forming part 6 forward. As a result, the engagement of the hook of the front end of the above-mentioned projection 64 with the projection 27 of the guide plate 26 is released whereby the slot-forming part 6 can be detached from the main body 1 of the measurement apparatus.

Incidentally, in the above-mentioned constitutions as shown in FIG. 5a, the constitution comprising the hollow 16 to the screw 25 functions as an adjusting mechanism for conducting the adjustment of inclined angle (angle of incidence of light) of the optical axis of optical head 15 to the measurement reagent 8, and the adjustment of the distance between the optical head 15 and the measurement reagent 8, and also the adjustment of the spot diameter of the light on the measurement reagent 8.

When the measurement reagent 8 is inserted from the slot 6 after attaching the slot-forming part 6 to the main body 1 of the measurement apparatus as mentioned above, the reagent-holding part of the measurement reagent 8 is positioned so as to position on the optical axis of the optical head 15 while the measurement reagent 8 is positioned so as to become parallel to the guide plate 26. Accordingly, when the support plate 17 is rotated, the inclined angle (angle of incidence of light) of the optical axis of the optical head 15 to the measurement reagent 8 can be changed. When the light-holding plate 24 is slid along the guide gutter 19, distance between the optical head 15 and the measurement reagent 8, and spot diameter of the light on the measurement reagent 8 can be changed.

In the measurement of stress, it is preferred that the above inclined angle, distance and spot diameter are appropriately adjusted by such adjusting mechanisms so that the measuring work is made optimum. Alternatively, when the preferred set values are different for each of the measurement reagents, it is necessary that the above-mentioned adjustment is appropriately carried out whenever the measurement reagent is changed.

Figure 7:
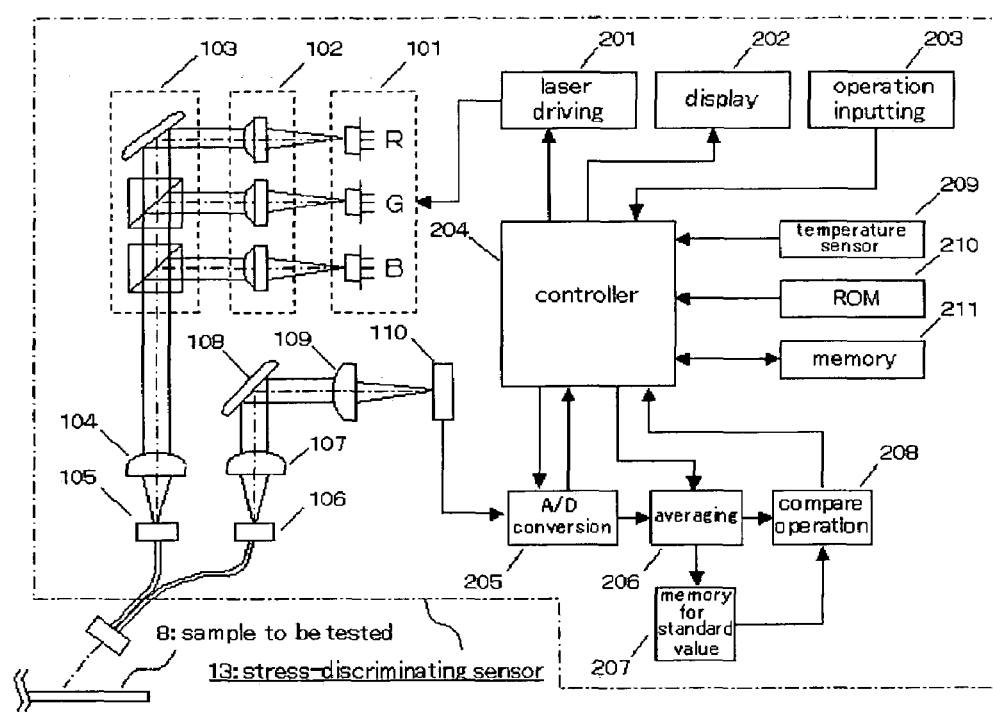
FIG. 7 shows an example of constitution of a stress discriminating sensor according to an embodiment.

Now the examples of constitution of the above-mentioned stress-discriminating sensor 13 will be illustrated by referring to FIG. 7. In the drawing, 101~110 are examples of constitution of an optical system while 201~211 are examples of constitution of a circuit system.

In the drawing, 101 is a semiconductor laser which emits the light of red (R), green (G) and blue (B), 102 is a collimator lens which converts the emitted light to parallel light, 103 is a mirror element which coincides the optical axes of the above-mentioned three lights (R, G and B), 104 is a convergent lens which focuses the above-mentioned lights to an incoming entrance of a light-coupling element 105 and 105 is a light-coupling element which is connected to one end of the above-mentioned optical fiber 14 and lets the above-mentioned lights come into the optical fiber 14.

106 is a light-coupling element which is connected to an end of the optical fiber introducing the reflected light from the measurement reagent 8, 107 is a convergent lens which makes the above-mentioned reflected light emitted from the light coupling element 106 into parallel light, 108 is a reflecting mirror, 109 is a convergent lens which focuses the above-mentioned reflected light onto a light detector 110 and 110 is a light detector which outputs an electric signal corresponding to the intensity of the focused reflected light.

201 is a laser-driving circuit which drives a semiconductor laser 101, 202 is a display part which comprises the above-mentioned display panel 4 and also outputs the display corresponding to the stress value calculated by the controller 204 and 203 is an operation-inputting part which comprises the above-mentioned operation button part 5 and also inputs the command corresponding to the operation button to the controller 204.

204 is a controller which controls each part and also calculates the stress value (degree of stress) on the basis of a result of compare operation by a compare operation part 208 and a temperature information from a temperature sensor 209 as well as a statistic information from ROM 210. The controller 204 has a clock circuit inside and measures the elapsed time after insertion of the measurement reagent 8 by such a clock circuit. Incidentally, details of process for detecting insertion of the measurement reagent 8 and operation for time-calculation by the clock circuit will be mentioned later.

205 is an A/D converter where analog electric signal from the light detector 110 is amplified and shaped to a waveform and, at the same time, analog electric signal is converted to digital signal with a predetermined sample period, 206 is an averaging part where sampling values supplied from the A/D converting circuit 205 within a predetermined period are averaged to calculate the mean value within said period, 207 is a standard value memory where the mean value calculated by the averaging part 206 upon insertion of the above-mentioned standard paper (in white color) into the slot 6 is held as a standard value and 208 is a compare operation part where the mean value calculated by the averaging part 206 upon measurement of the stress and the standard value held in the standard value memory 207 are compared and the difference between the two is calculated.

209 is a temperature sensor where it is placed near the inserting part of the measurement reagent 8 (omitted in FIG. 5 and FIG. 6) to detect the temperature near said inserting site and the detected result is supplied to a controller 204, 210 is a ROM (read-only-memory) where a conversion table for converting the result of compare operation by the compare operation part 208 to a stress value, a correction table for correcting the stress value of said conversion table by the temperature information and statistic data such as information concerning the progress of the above-mentioned compare operation result to the reaction time are held and 211 is a memory which memorizes the measurement history of the stress value.

Now, operation of such stress-discriminating sensor 13 will be illustrated.

Firstly, operation at the above-mentioned initial operation (adjustment of zero point) will be illustrated. When a standard paper (in white color) is inserted from the slot 6 and a button for the initial setting is operated in the above-mentioned initial operation, a semiconductor laser (R) among the semiconductor lasers 101 is driven for a predetermined time T whereupon light (R) in red color is emitted. The light (R) is irradiated to the standard paper via an optical system comprising the components from the collimator lens 102 to the light-coupling element 105 and also via the optical fiber 14 and the optical head 15 of the above-mentioned FIG. 5*a*. When the light (R) is irradiated to the standard paper, said light (R) is scattered and reflected by the standard paper and a part of it moves backward in the optical path of the above optical head 15 and optical fiber 14 and is emitted from the light-coupling element 16. It is then focused on the light detector 110 via an optical system comprising the component from the convergent lens 107 to the focusing lens 109.

The light detector 110 receiving such a reflected light sends electric signal corresponding to the intensity thereof to the A/D converter 205. During the above-mentioned time T, the A/D converter repeats sampling of said electric signal and sends it to the averaging part 206. The averaging part 206 averages said sampling values within a period T and the calculated result thereof is sent to the standard value memory 207. The standard value memory 207 keeps said mean value as a standard value for the light (R). As a result, setting of the initial value for the light (R) is finished.

When a standard value for the light (R) is thus maintained, a semiconductor laser (G) is then driven for a predetermined period T whereupon light (G) in green color is emitted. Then, as same as above, reflected light of the light (G) is received by the light detector 110 and electric signal corresponding to the intensity thereof is outputted. Such an electric signal is processed as same as above whereby a standard value for the light (G) is maintained in the standard memory 207. As a result, setting of the initial value for the light (G) is finished. After that, a semiconductor laser (B) is driven for a predetermined period T and, as same as above, a standard value for the light (G) is maintained in the standard memory 207. Thus, initial setting to all colors is completed.

Now, operation during the measurement of stress will be illustrated.

When the above-mentioned initial setting operation is finished, the laser driving part 201 drives the semiconductor laser 101 so that the semiconductor lasers (R), (G) and (B)

are repeatedly driven one after another for the above-mentioned period T per each light. Thus, from the semiconductor laser 101, various colors are emitted with a repeated cycle of 3T. In such a state (state of waiting for the measurement), light of each color mentioned above is emitted to the guide 61 of the slot-forming part 6 as shown in the above FIG. 6. However, the back plate 63 is not placed onto a bottom of the guide at the site (near the notch 62 of FIG. 6) of the guide 61 to which light is irradiated and, therefore, the light is not reflected by the guide 61, so that the reflected light is not focused to the light detector 110 of FIG. 7. Accordingly, value of the sampling value supplied to the controller 204 from the A/D converter 205 is nearly zero.

When the measurement reagent 8 is inserted from the slot 6 after that, light of each color mentioned above is reflected by the front end of the measurement reagent and the reflected light is focused to the light sensor 11. As a result, the content of the sampling value supplied to the controller 204 from the A/D converter 205 rises to a predetermined value from zero. The controller 204 detects the insertion of the measurement reagent by the rise of the sampling value as such and then controls each part so as to conduct the stress measuring operation.

To the laser driving circuit 201, light of each color is repeatedly emitted for the period T per each light as same as above. Such light of each color is absorbed, scattered and reflected by the reagent-holding part of the measurement reagent 8 and the mean value of intensity of the reflected light at each period T is compared with the standard value for said color at the compare operation part 208. The result of the compare operation for the light of the color is successively supplied to the controller 204.

Thus, for example, when the above-mentioned period T arriving after detection of the insertion of the above measurement reagent 8 by the controller 204 is T1, T2, T3, T4, . . . , color of the emitted light during that timing period is R →G →B →R . . . , mean value of the intensity of the reflected light at that time is A1, A2, A2, A4, . . . and the result of the compare operation thereof is D1, D2, D3, D4, . . . , then the mean value A1 is compared with the standard value of the light (R) in the period T1 and its difference is outputted to the controller 204 as D1. Similarly, in the period T2, the mean value A2 is compared with the standard value of the light (G) and its difference is outputted to the controller 204 as D2 and, in the period T3, the mean value A3 is compared with the standard value of the light (B) and its difference is outputted to the controller 204 as D3.

In the controller 204, a stress value is calculated on the basis of a series of compare operation results D1, D2, D3, D4, . . . , which are thus transmitted, temperature information from the temperature sensor 209 and the correction table (temperature and elapsed time) and the stress conversion table in the ROM 210. To be more specific, the corrected stress value to be referred to is determined on the basis of elapsed reaction time and temperature at the timing of T1, T2, T3, T4, . . . each, by referring to the statistic data and correction table memorized in the ROM 210 above-mentioned. Then the stress value corresponding to said compare operation results (D1, D2, D3, D4, . . . ) is read out from the conversion table followed by being added thereto or being deduced therefrom the above-mentioned correction value, whereupon the stress value for each timing is calculated. The stress value thus calculated is subjected to an averaging process for a predetermined period (such as T1~T99) and said averaged stress value is decided as the final stress value in said measurement.

For example, when the relation between the stress value and the compare operation result for a set of lights R, G and B are memorized in the above ROM 210 as a conversion table, the stress value corresponding to a combination of the compare operation results D1, D2 and D3 is read out from the conversion table. Then the stress correction value above-mentioned is added to or deducted from the stress value whereupon the stress value S1 for the periods T1~T3 is calculated. Timing for deciding the above stress correction value is a timing of intermediary T2, for example. Similarly, the stress values S2, S3, . . . S33 for the period T4~T6, T7~T9, . . . T97~T99 are calculated. Then the stress values for S1~S33 are averaged and used as the final stress value in said measurement.

Alternatively, when the result of the compare operation itself is adopted as the stress value, D1~D3 are added to calculate the stress value and the stress correction value above-mentioned is added thereto or deducted therefrom whereupon the stress value S1 for the period T1~T3 is calculated. Similarly, the stress values S2, S3, . . . S33 for the periods T4~T6, T7~T91, . . . T97~T99 are calculated and those stress values for S1~S33 are averaged and used as a stress value for said measurement. In that case, the above-mentioned conversion table becomes unnecessary. It is however necessary that the processing process for conducting the above-mentioned operation is memorized in the ROM 210. Incidentally, in the operation processing, various operation processing for discriminating the degree of color development of the measurement reagent may be adopted in addition to the addition of D1~D3 mentioned above.

The stress value thus determined is displayed on the display part 202. At the same time, it is also recorded in the memory 211 as a private measurement history. Incidentally, the measurement history memorized in the memory 211 can be appropriately read out and displayed on the display 202 by operating the operation inputting part 203.

The stress values displayed on the display part 202 is showed by the form of being displayed as specific numerals as well as being displayed in such a manner that the stress values are classified into groups of predetermined numeral range and is displayed by corresponding groups by means of cartoon (static image or animation) or letters.

Now, various modified examples of the stress measurement apparatus will be illustrated by referring to the drawings.

Example 5

Figure 8:
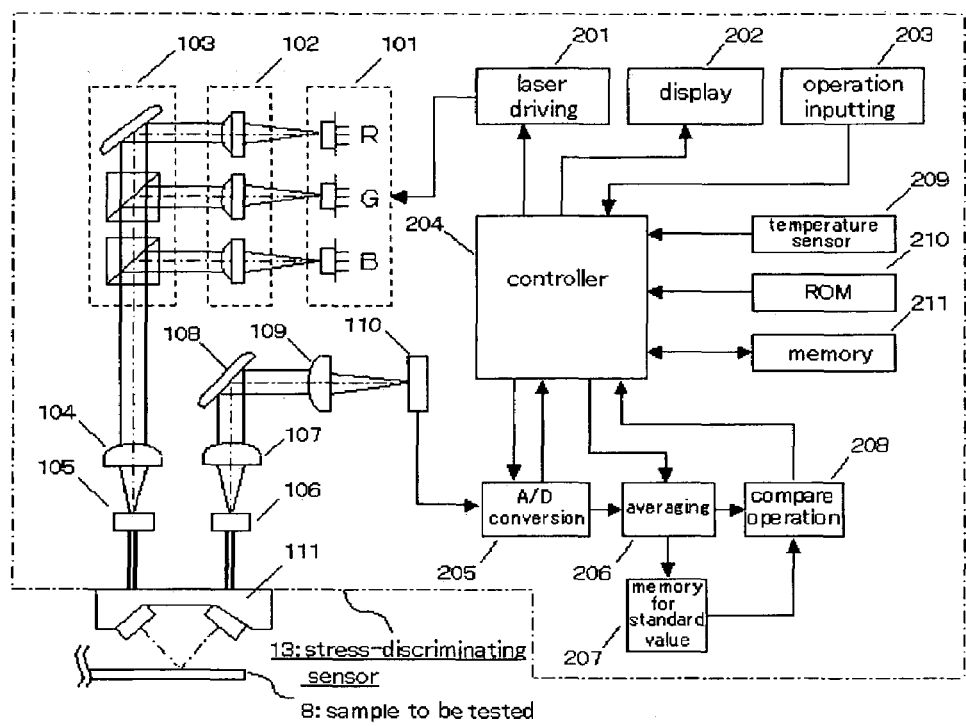
FIG. 8 shows another example of constitution of a stress discriminating sensor according to an embodiment.

FIG. 8 is a modified example of an optical head 15. In this example, an optical head 111 of a facing type is arranged in place of the above-mentioned optical head 15. Thus, the emitting end and the in-coming end of the optical head 111 are arranged in such a manner that an optical axis of the emitting light and that of the reflected light are coordinated and the inclined angle of both axes to the measurement reagent 8 is made identical. As a result, reflected light from the measurement reagent 8 can be introduced much more to the light detector 110 and, therefore, the operation output from the compare operation part 208 can be made more dynamic. Accordingly, precision for the stress discrimination can be further enhanced.

Example 6

Figure 9:
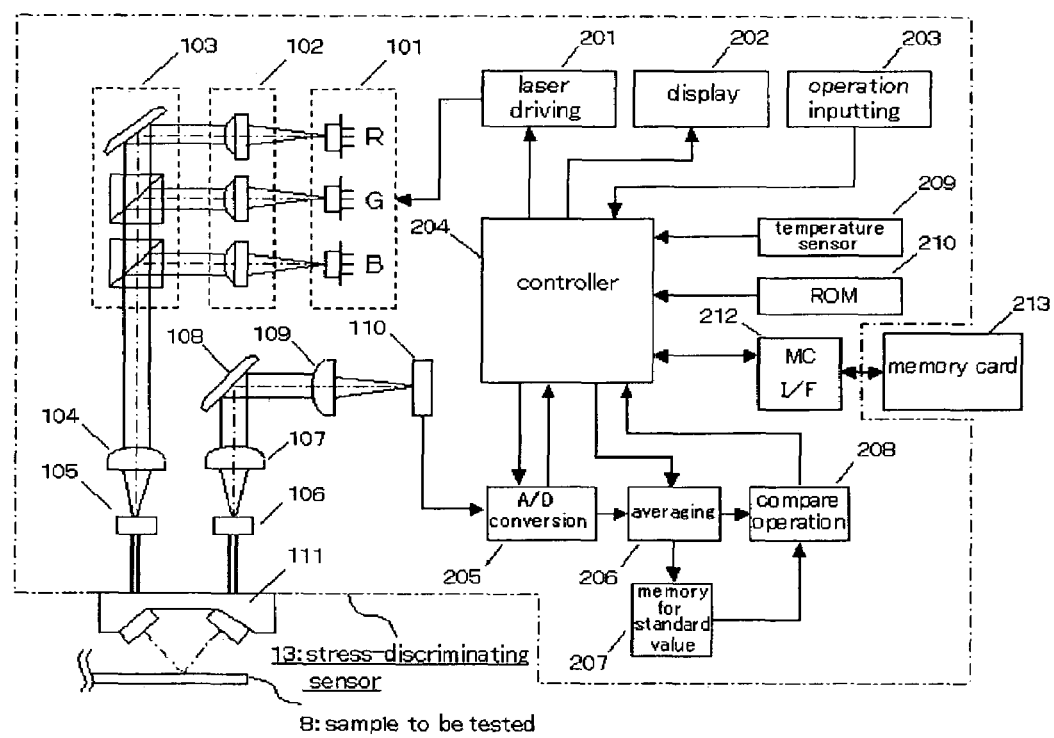
FIG. 9 shows another example of constitution of a stress discriminating sensor according to an embodiment.

FIG. 9 is a modified example of the above-mentioned memory 211. In this example, a memory card interface 212 and a memory card 213 are arranged in place of the above-mentioned memory 211. The above-mentioned stress measurement history is memorized in a memory card 213 via the memory card interface 212. The memory card 213 can be freely attached thereto and detached therefrom. Therefore, when the memory card 213 is held by each person to be measured, the measurement history can be controlled only by each person. It is also possible that one stress measurement apparatus can be used by plural persons.

Example 7

Figure 10:
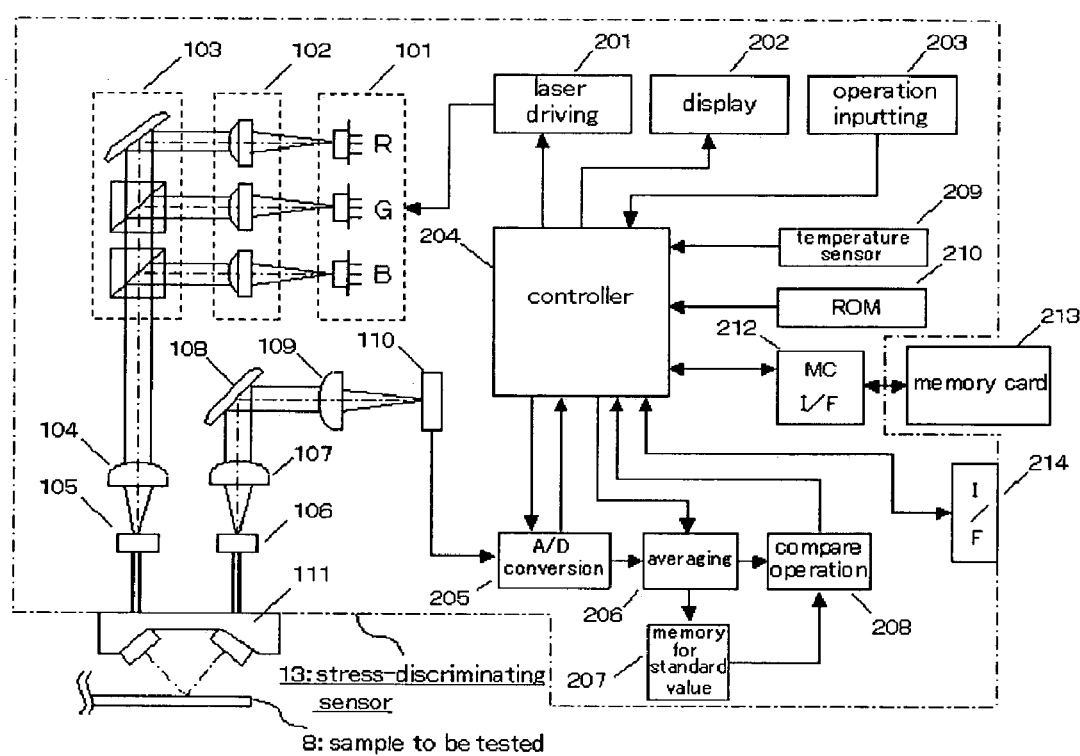
FIG. 10 shows another example of constitution of a stress discriminating sensor according to an embodiment.

FIG. 10 is an example where an interface 214 for transmitting to a personal computer is arranged. Said drawing shows an example where a memory card 213 is utilized as a medium for memorizing the measurement history but, as shown in FIG. 8, it can be also applied to the case where a measurement history is memorized in a memory within the apparatus. The measurement history which is memorized in the memory card 213 or the memory 211 can be transmitted to a personal computer via the interface 214. As a result, it is now possible to process the transmitted history on a personal computer or to send the measurement history to medical institutions by attaching to a mail. Incidentally, it is also possible that a communication means such as telephonic conversation is arranged in place of arranging an interface to a personal computer Example 8

Figure 11:
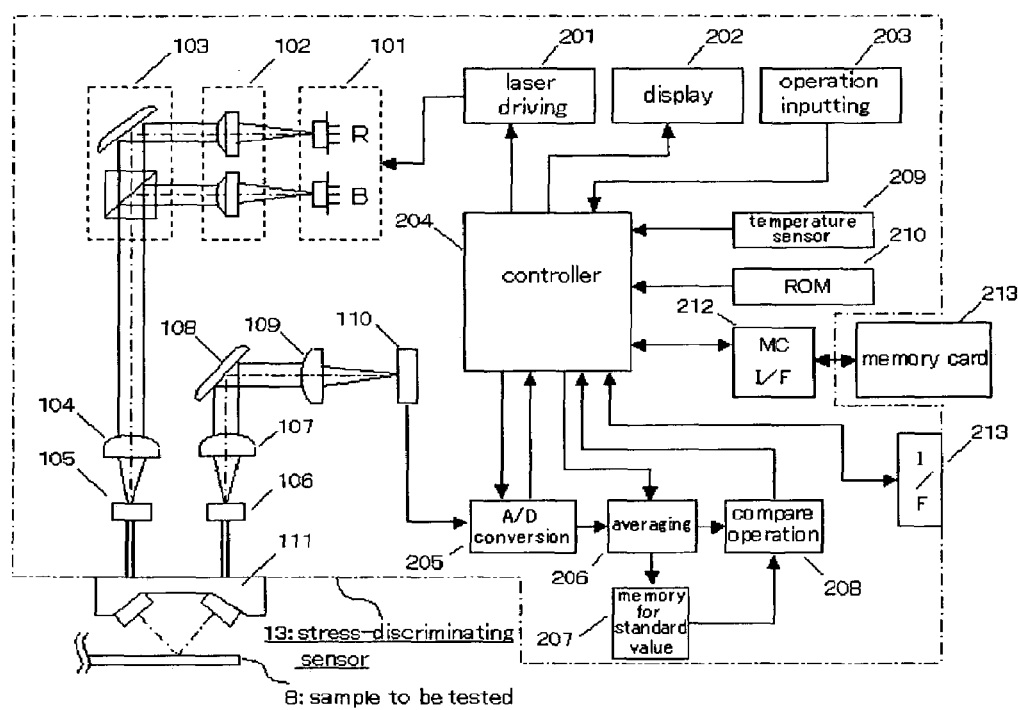
FIG. 11 shows another example of constitution of a stress discriminating sensor according to an embodiment.
Figure 12:
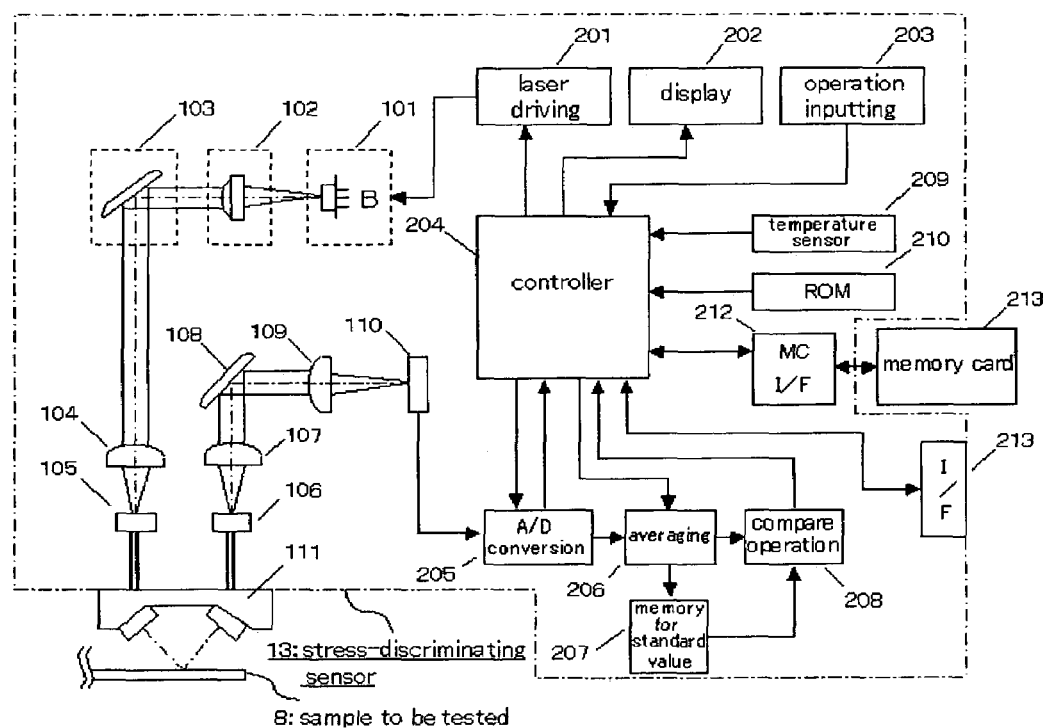
FIG. 12 shows another example of constitution of a stress discriminating sensor according to an embodiment.

FIG. 11 and FIG. 12 are modified examples of the semiconductor laser 101. In an example of FIG. 11, light only in red and blue colors is emitted from the semiconductor laser 101. In an example of FIG. 12, light only in blue color is emitted from the semiconductor laser 101. They are preferably used in the case where the color development of the measurement reagent by the reaction with saliva is in yellow. When the color development is in yellow, light in blue color is easily absorbed by the measurement reagent whereby a big change is noted in the result of compare operation to light in blue color. Therefore, it is now possible to calculate the degree of stress in a relatively good precision even in the case of using only blue color light, a combination of blue color light and red color light and a combination of blue color light and green color light. However, when the light only in red and green colors is utilized in case the color development of the measurement reagent is in yellow, precision of the discrimination of degree of stress lowers. That is because, since absorption of those colors by the measurement reagent is little, result of the compare operation does not change dynamically. Accordingly, when one or two color(s) among the three colors is/are used, it is preferred to set a combination or the like so as to contain light which can be in a complementary color to the color development of the measurement reagent.

As hereinabove, various embodiments concerning the present invention are illustrated, although the present invention is not limited to such embodiments. For example, although degree of stress is visually outputted on a display panel of the display part 2 in the above examples, it is also possible to adopt a display of degree of stress by means of voice or a display by means of print out instead of the above examples or together with the above ones.

Further, embodiments of the present invention can be variously and appropriately changed within a scope of the technical idea of the present invention.

Industrial Applicability

As mentioned hereinabove, in accordance with the present invention, there is provided a reagent for measuring amylase activity by an enzymatic method where a modified oligosaccharide which is a substrate is carried on a support. When amylase activity is measured using this reagent, it is possible to measure the amylase activity quite conveniently and quickly, whereby an art can be established where stress of a subject can be discriminated at that place within short time.

The invention claimed is:

1. A method for measuring amylase activity in saliva, comprising contacting a reagent for measuring amylase activity to saliva containing amylase, and measuring quantitatively with a color discriminating sensor a labeling substance which is liberated from a substrate,
   wherein said reagent comprises at least a modified oligosaccharide which is a substrate carried on a support;
   wherein said modified oligosaccharide is an oligosaccharide selected from G2, G3, G4, G5, G6, and G7, and the reducing end of the oligosaccharide is modified by a chromogen;
   wherein a light-emitting body provides a light source directed at the substrate;
   and said measuring quantitatively comprises measuring an intensity of light reflected from the substrate or transmitted through the substrate and outputting an electric signal corresponding to the intensity of the reflected light or transmitted light.

2. The method for measuring amylase activity according to claim 1, wherein the saliva is human saliva.

3. The method for measuring amylase activity according to claim 1, comprising measuring the color reaction of the labeling substance, which is liberated from the substrate, by the color discriminating sensor.

4. The method for measuring amylase activity according to claim 1, comprising measuring the reflected light from the support or the transmitted light through the support.

5. The method for measuring amylase activity according to claim 3, comprising providing a light-emitting body as a light source and the light-emitting body is a light-emitting diode.

6. The method for measuring amylase activity quantitatively with the color discriminating sensor according to claim 3, wherein the color discriminating sensor is adjusted so that an angle for measuring reflected light is 0~45°, a distance from the support to be measured is 10 mm~30 mm and a spot diameter of light on the reagent for measuring amylase activity is 1 mm~5 mm.

7. The method for measuring amylase activity according to claim 1, wherein said color discriminating sensor has the following functions:
   (1) measuring a color reaction of a labeling substance liberated from the reagent for measuring amylase activity,
   (2) measuring reflected light from the support or transmitted light from the support,
   (3) providing a light-emitting body as a light source selected from a light-emitting diode, a laser, a halogen lamp and a tungsten lamp, and
   (4) providing a means for measuring light reflected from the substrate at an angle of 0~45° and a distance of 10 mm~30 mm, and wherein a spot diameter of light on the reagent for measuring amylase activity is 1 mm~5 mm.

8. The method according to claim 1, wherein the support is an organic or inorganic carrier that is water-insoluble.

9. The method according to claim 1, wherein the shape of the support is a thin film.

10. The method according to claim 9, wherein thickness of the thin film is 100 μm~500 μm.

11. The method according to claim 9, wherein the thin film is in white color.

12. The method according to claim 9, wherein diffused reflection of the thin film is controlled.

13. The method according to claim 1, wherein an amount of the modified oligosaccharide carried on the support is that which corresponds to the amount obtained by dipping the support into a solution containing 2 mmol/L~500 mmol/L of the modified oligosaccharide substrate for about 1 to 5 minute(s).

14. The method according to claim 1, wherein the chromogen is selected from 4-nitrophenol (PNP), 2-chloro-4-nitrophenol (CNP) and 2,4-dichlorophenol ($Cl_2P$).

15. The method according to claim 1, wherein the modified oligosaccharide is selected from the following: 2-chloro- 4-nitrophenol-4-O-β-D-galactopyranosyl maltoside (hereinafter, referred to as GAL-G 2-CNP), GAL-G 4-CNP, GAL-G5-CNP, G5-CNP, G6-CNP, G7-CNP, G5-PNP and G7-PNP.

* * * * *